United States Patent [19]

Spector et al.

[11] Patent Number: 4,758,572
[45] Date of Patent: Jul. 19, 1988

[54] ANTIVIRAL COMBINATIONS

[75] Inventors: Thomas Spector, Durham; Devron R. Averett, Raleigh; Donald J. Nelson, Hillsborough, all of N.C.

[73] Assignee: Burroughs Wellcome Co., Research Triangle Park, N.C.

[21] Appl. No.: 22,542

[22] Filed: Mar. 5, 1987

Related U.S. Application Data

[63] Continuation of Ser. No. 635,307, Jul. 27, 1984, abandoned.

[30] Foreign Application Priority Data

Jul. 28, 1983 [GB] United Kingdom ............... 8320308

[51] Int. Cl.$^4$ ............................................. A61K 31/52
[52] U.S. Cl. ................................................. 514/265
[58] Field of Search ..................................... 514/265

[56] References Cited

U.S. PATENT DOCUMENTS

| | | | |
|---|---|---|---|
| 2,678,295 | 5/1954 | Goreau et al. | 564/20 X |
| 3,591,636 | 7/1971 | Houlihan et al. | 564/20 X |
| 3,712,914 | 1/1973 | Tiller | 564/20 X |
| 3,776,942 | 12/1973 | Miller et al. | 564/21 X |
| 4,199,574 | 4/1980 | Schaeffer | 514/262 |
| 4,355,032 | 10/1982 | Venheyden et al. | 514/262 |
| 4,447,427 | 5/1984 | Klayman et al. | 564/331 X |
| 4,495,190 | 1/1985 | Hagberg et al. | 514/262 |

FOREIGN PATENT DOCUMENTS 1058835  2/1967  United Kingdom .

OTHER PUBLICATIONS

Shipman, Jr. et al., Antimicrobial Agents and Chemotherapy, Apr. 1981, pp. 682–685.
Jerome A. Streifel and Stephen B. Howell, Proc. Natl. Acad. Sci., vol. 78, No. 8, Aug. 1981, pp. 5132–5136.
Richard G. Moran et al, Biochemical Pharmacology, vol. 31, No. 18, 1982, pp. 2929–2935.
R. Wigand and M. Hassinger, Med. Microbiol. Immunol., 168, 179–190 (1980).
Dobek et al., Arzheim Forsch. Drug Res., 33 (1983), pp. 1583–1591.
French et al., J. Med. Chem., vol. 17, No. 2, (1974), pp. 172–180.
Cory et al., Cancer Research, vol. 40, (1980), pp. 3891–3894.
Neidhart et al., Cancer Treatment Reports, vol. 64, Nos. 2 & 3, (1980), pp. 251–255.
Clark et al, J. Med. Chem., vol. 22, (1979), p. 1369.
Elford et al., Cancer Research, vol. 39, (1979), pp. 844–851.
Kaufman et al., Cancer Chemotheraphy Reports, Part 1, vol. 59, No. 5, (1975), pp. 1007–1014.
Cory et al., Cancer Research, vol. 36, (1976), pp. 3166–3170.
Cory et al., Biochemical Pharm., vol. 28, (1979), pp. 861–871.
Brockman et al., Cancer Research, vol. 30, (1970), pp. 2358–2368.
Cheng et al., Antimicrobiol Agents and Chemotheraphy, vol. 20, No. 3, (1981), pp. 420–423.
De Clercq et al., Proc. Natl. Acad. Sci., vol. 76, No. 6, (1979), pp. 2947–2951.
Grant et al., Biochem. Pharm., vol. 31, No. 6, (1982), pp. 1103–1108.
De Clercq et al., Biochem. Pharm., vol. 28, (1979), pp. 3249–3254.
A. Holmgren, Current Topics in Cellular Regulation, 19, (1981), 47–77.
Alan C. Sartorelli et al, Adv. Enz. Reg. 15, (1977), 117–139.

Primary Examiner—Stanley J. Friedman
Attorney, Agent, or Firm—Donald Brown

[57] ABSTRACT

Synergistic combinations of nucleoside analogues, which are converted to viral DNA polymerase inhibitors through the action of at least one virus-induced enzyme, and thiosemicarbazone ribonucleotide reductase inhibitors are especially useful in combatting herpes virus infections.

6 Claims, No Drawings

ANTIVIRAL COMBINATIONS

This application is a continuation of application Ser. No. 06/635,307, filed 07/27/84, now abandoned.

The present invention relates to new antiviral combinations for the chemotherapeutic treatment of virus infections, especially viruses of the herpes group.

During the last ten years or more various antiviral chemotherapeutic agents have been developed for clinical evaluation. A problem with the development of such agents is that, unlike bacteria, viruses are not free-living organisms and are dependent for replication on the life processes of the host cell which they are infecting. It is therefore highly desirable for the antiviral agent to exert its effect specifically on the replicative processes of the virus rather than on the corresponding processes of normal (non-infected) cells. The antiviral agents so far developed act via a variety of mechanisms to exert their antiviral effects, such mechanisms involving inhibition of different stages in the process of viral replication in the host cells.

One particular stage of replication at which the virus is susceptible to inhibition is the stage of nucleic acid replication, i.e., the production of DNA from DNA or RNA from RNA (depending on whether the virus is a DNA or an RNA virus respectively) where the viral DNA or RNA acts as a template for the production of new DNA or RNA respectively. In the case of DNA viruses, the production of new viral DNA involves the interaction of the enzyme DNA polymerase with the constituent nucleotides (specifically deoxyribonucleotides) which act as building blocks for the new DNA. Antiviral action at this stage generally involves the use of "fraudulent" or deleterious nucleotides which mimic the normal viral materials and either compete for DNA polymerase or are incorporated into the viral DNA chain to make it non-functional.

These "fraudulent" or deleterious nucleotides comprise a nucleoside triphosphate derived from a nucleoside analogue which is converted by enzymes first into the monophosphate and then subsequently into the diphosphate and finally into the triphosphate. An example of this type of antiviral is acyclovir, i.e., 9-(2-hydroxyethoxymethyl)guanine, which is related to the naturally occurring nucleoside, guanosine, but which contains an acyclic side-chain in the 9-position compared with a cyclic sugar residue in this position in guanosine. The antiviral mechanism of action of acyclovir involves first its conversion to acyclovir monophosphate by the enzyme thymidine kinase, which is specific to herpes-infected cells. Once formed, acyclovir monophosphate is converted by normal cellular enzymes (kinases) via the diphosphate to acyclovir triphosphate (ACVTP). Acyclovir triphosphate serves as in inhibitor of viral DNA polymerase since it resembles the natural nucleotide substrate, deoxyguanosine triphosphate (dGTP), and as a result competes with dGTP for binding to the DNA polymerase and thus competitively inhibits the effectiveness of the enzyme and consequently viral replication. Whe ACVTP acts as a substrate for DNA polymerase it becomes incorporated into the viral DNA chain but since it lacks the 3'-hydroxyl group normally present on the cyclic sugar moiety, it acts as a DNA chain terminator. It also apparently inactivates the viral DNA polymerase. Thus, viral replication is prevented.

Thus, the antiviral effect of acyclovir, and related compounds which operate via an analogous mode of acton, involves competitive inhibition and apparent inactivation of the viral DNA polymerase.

A disadvantageous aspect of a competitive inhibitor is that the normal substrate may accumulate and become more effective in competitively blocking the binding of the inhibitor. In this manner, the build up of for example dGTP may hinder the binding of ACVTP to the polymerase and thereby prevent subsequent termination of viral DNA processing.

We have now discovered that the use of a ribonucleotide reductase (RR) inhibitor in conjunction with an antiviral agent of the above described type surprisingly increases the formation of antiviral (triphosphate) compound in addition to decreasing the pool of dGTP and hence the ratio of antiviral (triphosphate) compounds to the competiting viral deoxynucleotide substrate of DNA polymerase (e.g., dGTP) is greatly improved. The binding of the antiviral compound to the viral DNA polymerase is thus enhanced.

The net result is that the use of a RR inhibitor in combination with an antiviral of the above described type results in a surprising synergistic increase in antiviral efficacy in comparison with the individual antiviral effects of the components of the combination. The present invention has been found to be particularly applicable to the treatment of herpes viruses, as described below.

According to a feature of the present invention there is provided a combination of (a) an antiviral compound which is converted in vivo by virus-induced enzymes to an inhibitor of, or an alternative substrate for, viral DNA polymerase, and (b) a thiosemicarbazone ribonucleotide reductase inhibitor, components (a) and (b) of the combination being employed in a ratio whereby a synergistic antiviral effect is achieved.

The term "synergistic antiviral effect" is used to denote an antiviral effect which is greater than the purely additive effects of the individual above-defined components of the combination.

The present invention also provides the use of the above-defined combination for the treatment or prophylaxis of viral diseases in the human and animal body.

The invention further provides a method for the treatment of viral diseases in a human or animal body which comprises administering to the human or animal body an effective amount of a combination as defined above. It will be appreciated that in accordance with the present invention the antiviral compound and the RR inhibitor may be administered simultaneously or sequentially. In the latter case, however, the components of the combination are administered within a sufficiently short interval to ensure that a synergistic antiviral effect is achieved.

The present invention also provides:

(a) A method of therapeutically increasing the pool size of a deleterious substrate and/or inhibitor of viral DNA polymerase in a mammal having a viral infection and receiving an antiviral compound which depends on viral-induced enzymes of the virus for conversion to said deleterious substrate and/or inhibitor in the mammal, the improvement of administering to said mammal an effective, non-toxic ribonucleotide reductase deleterious substrate and/or inhibitor in an amount effective for increasing the pool of said inhibitor and/or deleterious substrate of viral DNA polymerase in said mammal; and (b) A method of potentiating in a mammal having a viral infection the antiviral activity of an antiviral compound being administered to said mammal and which depends on a viral-induced enzyme for conversion to a deleterious substrate and/or inhibitor of viral DNA polymerase which comprises administering to said mammal an effective, non-toxic potentiating amount of a ribonucleotide reductase inhibitor.

An advantage of the combination according to the invention is that it enables one to obtain an improved antiviral efficacy at a particular dosage of the antiviral compound (compared with the compound used alone) thereby improving the therapeutic index of the compound. Thus for example, the combination may be used to treat conditions which would otherwise require relatively large dosages of the antiviral compound at which toxicity problems may occur.

The combination according to the invention is especially applicable to the treatment of herpes simplex types 1 and 2 but other herpes viruses can also be treated, for example, varicella zoster, cytomegalovirus and Epstein-Barr virus.

With regard to the antiviral compound, this can be selected from any compound that is converted in vitro by virus-induced enzymes. Such compounds are generally substrates for an appropriate kinase enzyme of viral origin which phosphorylates the compounds to form initially a monophosphate which is then phosphorylated (also by kinase enzymes of either viral or cellular origin) first to the diphosphate and finally to the triphosphate which serves as the DNA polymerase inhibitor. The use of an antiviral compound that is selectively phosphorylated by viral enzymes rather than by cellular enzymes provides a greater concentration of the phosphorylated material in infected cells than in non-infected cells, and thus provides a more selective antiviral effect. It is also preferred to use an antiviral compound that is not only a DNA polymerase inhibitor but is also, when incorporated into the viral DNA chain, a chain terminator and, possibly, an inactivator of the viral DNA polymerase.

Thus, for example, acyclovir, as mentioned above, is converted by virus-coded thymidine kinase (but not to any substantial extent by cellular thymidine kinase) to the monophosphate which is then converted to the triphosphate via the diphosphate by cellular enzymes. Acyclovir is also a DNA chain terminator. The mechanism of acyclovir and other antiviral nucleoside analogues is described by de Clerque in "New Trends in Antiviral Chemotherapy", *Archives Internationale de Physiologie et de Biochimie*, 1979, 87(2), pages 353–395.

The antiviral compound employed in the combinations according to the invention may be selected for example from acyclovir and analogues thereof, e.g., those compounds of formula

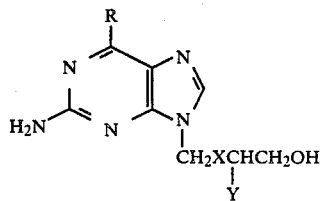

(wherein X is oxygen or sulphur, R is hydrogen, hydroxy or amino and Y is hydrogen or hydroxymethyl) and physiologically acceptable salts and esters thereof.

In addition to acyclovir, examples of preferred compounds of formula (I) for use in the present invention include:

9-[2-hydroxy-1-hydroxymethylethoxy)methyl]guanine as well as prodrugs that are converted in vivo into the above compounds, e.g. 2-amino-9-(2-hydroxyethoxymethyl)adenine, 9-[(2-hydroxy-1-hydroxymethylethoxy)methyl]-2,6-diaminopurine, and 2-amino-9-(2-hydroxyethoxymethyl)purine.

Alternatively, the antiviral compound may be a compound of formula

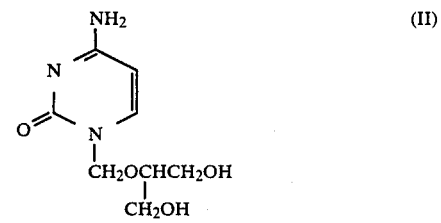

namely 1-[2-hydroxy-1-(hydroxymethyl)ethoxymethyl]cytosine or a physiologically acceptable salt thereof.

The thiosemicarbazone RR inhibitor is preferably a compound of formula

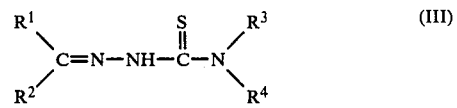

(wherein $R^1$ represents an unsubstituted thienyl or pyridyl group or a thienyl, pyridyl or phenyl group substituted by at least one (e.g., 1, 2 or 3) substituent selected from $C_{1-6}$ alkyl (e.g., methyl or ethyl), $C_{1-6}$ alkoxy (e.g., methoxy or ethoxy), hydroxy or halo (chloro, bromo, iodo or fluoro) radicals;

$R^2$ represents a hydrogen atom or a $C_{1-6}$ alkyl (e.g., methyl) group; $R^3$ represents a hydrogen atom, a $C_{1-6}$ alkyl (e.g., methyl or ethyl) group, a group of formula Z-X (wherein Z represents a $C_{1-4}$ straight or branched alkylene group and X represents a $C_{1-6}$ alkoxy group, a phenyl group substituted by at least one $C_{1-6}$ alkoxy group, or a 5- or 6-membered heterocyclic ring containing at least one heteroatom selected from oxygen, nitrogen and sulphur, e.g., a 2-, 3- or 4-pyridyl, morpholino or 2-,3- or 4-furanyl group), or a group of formula

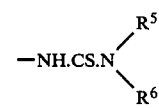

(wherein $R^5$ and $R^6$, which may be the same or different, each represent hydrogen atom or $C_{1-6}$ alkyl group); and $R^4$ represents a hydrogen atom or a $C_{1-6}$ alkyl group); or $R^3$ and $R^4$ together with the nitrogen atom to which they are attached form a 3- to 7-membered alkyleneimino ring (optionally containing a double bond) or a homopiperazino, piperazino or morpholino group optionally containing 1,2 or 3 substituents selected from $C_{1-14}$ alkyl, hydroxy, phenyl and benzyl.

Certain of the RR inhibitors of formula (III) above also represent preferred compounds for use in the combinations according to the invention, namely those of formula (I) wherein $R^1$ represents a thienyl or pyridyl group or a phenyl group substituted by at least one hydroxy group and optionally by at least one $C_{1-6}$ alkyl group or halogen;

$R^2$ represents a hydrogen atom or a $C_{1-6}$ alkyl group;

$R^3$ represents a group of formula Z-X (wherein Z represents a $C_{1-4}$ straight or branched alkylene group and X represents a phenyl group substituted by at least one $C_{1-6}$ alkoxy group, or a 5- or 6-membered heterocyclic ring containing at least one heteroatom selected from oxygen, nitrogen and sulphur) or group of formula

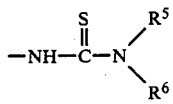

(wherein $R^5$ and $R^6$ are as defined above); or (providing $R^1$ is a phenyl group as defined above) a $C_{1-6}$ alkyl group; and $R^4$ represents a hydrogen atom or a $C_{1-6}$ alkyl group.

Examples of preferred compounds of formula (III) include 2-acetylpyridine 4-(2-morpholinoethyl)thiosemicarbazone 2-acetylpyridine 4-(3,4,5-trimethoxybenzyl)thiosemicarbazone 2-acetylpyridine 5-(dimethylamino)thiocarbonylthiocarbonohydrazone 2-acetylthiophene 5-(dimethyltiocarbamoyl)thiocarbonohydrazone 2-hydroxybenzaldehyde 4,4-dimethylthiosemicarbazone 2-hydroxy-5-methylacetophenone 4,4-dimethylthiosemicarbazone 2,3-dihydroxybenzaldehyde 4,4-dimethylthiosemicarbazone 2-acetylpyridine 4-[2-(2-pyridyl)ethyl]thiosemicarbazone 2-hydroxy-5-fluoroactophenone 4,4-dimethylthiosemicarbazone These last-defined compounds represent a further feature of the present invention since they have been found to potentiate (in a synergistic manner) the antiviral effects of the antiviral compounds described above.

According to a further feature of the present invention we provide a process for the preparation of the above-defined compounds of formula (II) which comprises reacting a compound of formula

(wherein $R^1$ and $R^2$ are as defined above) with a compound of formula

(wherein $R^3$ and $R^4$ are as defined above).

The reaction is advantageously effected in an appropriate solvent medium, e.g. methanol, ethanol, 2-dichloroethane, if desired in the presence of glacial acetic acid.

The combinations according to the invention may be administered to the subject concerned in conventional manner. As indicated above, the antiviral compound and the RR inhibitor may be administered simultaneously (e.g. in a unitary pharmaceutical formulation) or separately (e.g. in separate pharmaceutical formulations). In general, the combinations may be administered by the topical, oral, rectal or parenteral (e.g., intravenous, subcutaneous or intramuscular) route. The dosage of the combination will depend on the condition being treated, the particular antiviral agent and RR concerned and other clinical factors such as the weight and condition of the patient and the route of administration of the compound. However for administration by the oral route a dosage of the antiviral compound of 1 to 100 mg/kg/day, preferably 10 to 40 mg/kg/day is generally sufficient. The amount of RR inhibitor in the combination will be determined from the amount of antiviral compound specified above and the desired ratio of antiviral compound to RR inhibitor.

For convenience, the antiviral compound and RR inhibitor are preferably administered in a unitary pharmaceutical formulation. Thus, the present invention further provides a pharmaceutical formulation comprising an antiviral compound which is converted by viral or cellular enzymes to an inhibitor of viral DNA polymerase, and a RR inhibitor, together with at least one pharmaceutical carrier or excipient, the antiviral compound and RR inhibitor being present in the formulation in a ratio whereby a synergistic antiviral effect is achieved.

The formulations include those suitable for oral, rectal, nasal, topical (including buccal and sublingual), vaginal or parenteral (including subcutaneous, intramuscular, intravenous, intradermal, intrathecal and epidural) administration. The formulation may conveniently be presented in unit dosage form and may be prepared by conventional pharmaceutical techniques. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

Formulations of the present invention suitable for oral administration may be presented as discrete units such as capsules, cachets or tablets each containing predetermined amounts of the active ingredients; as powders or granules; as solutions or suspensions in an aqueous liquid or a non-aqueous liquid; or as oil-in-water emulsions or water-in-oil liquid emulsions. A tablet may be made by compression or moulding, optionally with one or more accessory ingredients. Compressed tablets may be prepared by compressing in a suitable machine the active ingredients in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

For infections of the eye or other external tissues, e.g, mouth and skin, the formulations are preferably applied as a topical ointment or cream containing the antiviral active ingredient in an amount of, for example, 0.075 to 20% w/w, preferably 0.2 to 15% w/w and most preferably 0.5 to 10% w/w. When formulated in an ointment, the active ingedients may be employed with either paraffinic or a water-miscible ointment base. Alternatively, the active ingredients may be formulated in a cream with an oil-in-water cream base.

If desired, the aqueous phase of the cream base may include, for example at least 30% w/w of a polyhydric alcohol, i.e., an alcohol having two or more hydroxyl groups such as propylene glycol, butane-1,3,-diol, mannitol, sorbitol, glycerol and polyethylene glycol and mixtures thereof. The topical formulation may desirably include a compound which enhances absorption or penetration of the active ingredient through the skin or other affected areas. Examples of such dermal penetration enhancers include dimethylsulphoxide and related analogues.

The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/fat make up the so-called emulsifying ointment base which forms the oily dispersed phase of the cream formulations.

Emulsifiers and emulsion stabilisers suitable for use in the formulation of the present invention include Tween 60, Span 80, cetostearyl alcohol, myristyl alcohol, glyceryl mono-stearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredient. The antiviral active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavoured basis, usually sucrose and acacia or tragacanth; pastilles comprising the active ingredient in an inert basis such as gelatin and glycerine, or sucrose and acacia; and mouth washes comprising the active ingredients in a suitable liquid carrier. Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns which is administered in a manner in which snuff is taken, i.e., by rapid inhalation through the nasal passage from a container of the powder held close up to the nose. Suitable formulations wherein the carrier is a liquid, for administration as for example a nasal spray or as nasal drops, include aqueous or oil solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solution and suspensions may be prepared from sterile powders, granules and tablets of the kind previously described.

Preferred unit dosage formulations are those containing a daily dose or unit daily sub-dose, as herein above recited, or an appropriate fraction thereof, of the active ingredients.

It should be understood that in addition to the ingredients particularly mentioned above the formulations of this invention may include other agents conventional in the art having regard to the type of formulation in question, for example those suitable for oral administration may include flavouring agents.

ANTIVIRAL ACTIVITY (1) Examples of Mutual Enhancement of the Antiherpetic Activities of 2-Acetylpyridine-4-(2-morpholinoethyl)thiosemicarbazone (compound A) and Acyclovir (ACV).

| Compound | Addition | $ED_{50}^a$ ($\mu M$) |
| --- | --- | --- |
| ACV | none | 0.6 |
| ACV | 1 $\mu M$ Compound A | 0.02 |
| Compound A | none | 5 |
| Compound A | 0.2 $\mu M$ ACV | 0.7 |

$^a$Yield reduction assay with HSV type-1 H-29 Strain (2) Other compounds according to the invention were also found to provide enhanced antiviral activity in combination with acyclovir when tested as follows:

(a) Observed % Inhibition

Tissue culture dishes (60 mm) containing a confluent layer of Vero cells (African Green Monkey Kidney) were infected with about 200 infectious units per dish of the Patton strain of herpes simplex virus type 1. The dishes were incubated for a 60 minute absorption period at 37° C. The thiosemicarbazone, ACV or the thiosemicarbazone and ACV combination were dissolved in Eagle's minimal essential medium containing 2% heat inactivated fetal bovine serum and 0.5% human immune serum globulin. Five mL of this medium containing the individual inhibitors or the combination were added to the culture dishes. After a three day incubation at 37° C., the cells were fixed with 10% formalin and then stained with 0.8% crystal violet. Virus plaque formation was visualized with a dissecting microscope.

The % inhibition of virus plaque formation by the inhibitors alone and in combination was calculated by the following equation:

$$\% \text{ INHIBITION} = 1 - \frac{\text{no. plaques with inhibitor}}{\text{no. plaques without inhibitor}} \times 100$$

(b) Calculated % Inhibition

The theoretical % inhibition for the combination of inhibitors was calculated from the amount of reduction of plaque formation observed individually by the thiosemicarbazone and ACV in separate experiments. The following equation was used:

CALCULATED % INHIBITION=1−[(1-% i(ACV)/100)(1-% i(thiosemicarbazone)/100)]×100

Where % 1(ACV) and % i(thiosemicarbazone) are the percent inhibition observed individually by these compounds.

(c) In the above experiments, the observed % inhibition was found to be significantly higher than the calculated % inhibition.

EXAMPLES (a) RR Inhibitors

Preparation of Thiosemicarbazones

General procedure: The appropriate aldehyde or ketone (A) and 4-substituted thiosemicarbazide (B) were refluxed in the specified reaction medium until the reaction was complete. The solid product was collected by filtration of the cooled reaction mixture and was then purified by recrystallization from the specified solvent or by column chromatography on silica gel followed by recrystallization from the specified solvent.

A specific example is illustrated below.

2-Acetylpyridine 4-(2-morpholinoethyl)thiosemicarbazone

A mixture of 6.00 g (0.0294 mole) of 4-(2-morpholinoethyl)thiosemicarbazide, 3.91 g (0.0323 mole) of 2-acetylpyridine, 20 mL of 95% ethanol, and 0.4 mL of glacial acetic acid was heated under reflux for 1.25 hours. The mixture then stood overnight at room temperature. Colourless crystals were collected and recrystallised from 40 mL of 95% ethanol; yield 7.81 g (86%) of pale yellow crystals of 2-acetylpryridine 4-(2-morpholinoethyl)thiosemicarbazone, mp 167.5°–169° C.

Analysis for $C_{14}H_{21}N_5OS$. Calculated: C: 54.69, H: 6.89, N: 22.78. Found: C: 54.66, H: 6.86, N: 22.88.

Exceptions to the general procedure were the preparations of the thiocarbonylthiocarbonohydrazones:

2-Acetylpyridine 5-[(dimethylamino)thiocarbonyl]thiocarbonohydrazone

A mixture of 24.2 g (0.203 mole) of 4,4-dimethylthiosemicarbazide, 26.6 g (0.220 mole) of 2-acetylpyridine, 2.5 mL of glacial acetic acid, and 100 mL of 95% ethanol was refluxed for 1.5 hours. The mixture was incubated overnight at room temperature. Thick orange needles contaminated with a little light-coloured solid were collected, washed with 20 mL of ethanol, and while still damp were added to 450 mL of boiling methanol. After the orange needles dissolved (less than 10 minutes) the mixture was filtered, and the undissolved solid was boiled again with methanol (50 mL) for three minutes. The mixture stood for 0.25 hour at room temperature, then the yellow crystals were collected by filtration; yield 1.47 g (5%) of 2-acetylpyridine 5-[(dimethylamino)thiocarbonyl]thiocarbonohydrazone, mp 152.5° C., (evolved a gas, resolidified, and remelted at 175°–181.5°).

Analysis for $C_{11}H_{16}N_6S_2$. Calculated: C: 44.57, H: 5.44, N: 28.35. Found: C: 44.75, H: 5.52, N: 28.45.

2-Acetylthiophene 5-(N,N-dimethylthiocarbamoyl)thiocarbonohydrazone

A mixture of 2-acetylthiophene (5.04 g, 0.040 mol), 4,4-dimethylthiosemicarbazide (2.98 g, 0.025 mol), 95% EtOH (20 mL) and glacial HOAc (0.4 mL) was refluxed for 1 h. The resulting solution was allowed to stand overnight at ambient temperature. The crystals that had separated were subsequently collected by filtration, washed with boiling 95% EtOH (30 mL), and recrystallized from 95% EtOH; yield, 0.48 g (13%) of 2-acetylthiophene 5-(N,N-dimethylthiocarbamoyl)thiocarbonohydrazone, mp 161° C., then resolidified.

Analysis for $C_{10}H_{15}N_5S_3$. Calculated: C: 39.84, H: 5.02, N: 23.23, S: 31.91. Found: C: 39.86, H. 5.04, N: 23.16, S: 31.86.

The following equation applies to the Table shown below:

$$R^1-\overset{O}{\underset{\|}{C}}-R_2 + H_2NNHC\overset{S}{\underset{\|}{N}}\diagup^{R^3}_{R^4} \longrightarrow \underset{R^1-\overset{\|}{C}-R^2}{NNHCN\diagup^{R^3}_{R^4}\overset{S}{\|}}$$

A        B

| | | | | | PREPARATION OF THIOSEMICARBAZONES | | | | |
|---|---|---|---|---|---|---|---|---|---|
| $R^1$ | $R^2$ | $R^3$ | $R^4$ | Molar Ratio A/B | Reaction Medium | Reaction Time (hr) | Recrystallization Solvent | Yield (%) | mp (°C.) |
| 2-pyridyl | Me | H | −(CH$_2$)$_2$−N(morpholino) | 1.1 | 95% EtOH/2% glacial acetic acid | 1¼ | 95% EtOH | 86 | 167.5–169 |

-continued

PREPARATION OF THIOSEMICARBAZONES

| R¹ | R² | R³ | R⁴ | Molar Ratio A/B | Reaction Medium | Reaction Time (hr) | Recrystal- lization Solvent | Yield (%) | mp (°C.) |
|---|---|---|---|---|---|---|---|---|---|
| 2-pyridyl | Me | H | —(CH₂)₃—N(morpholino) | 1.9 | ClCH₂CH₂Cl | 3 | i-PrOH | 47 | 126.5–127 |
| 2-pyridyl | Me | H | —(CH₂)₂—(2-pyridyl) | 1.1 | 95% EtOH/5% glacial acetic acid | 1½ | Toluene | 71 | 125–127 |
| 2-pyridyl | Me | H | —(CH₂)₃—OMe | 1.0 | MeOH | 28½ | i-PrOH | 74 | 103–104 |
| 2-pyridyl | Me | H | —CMe₃ | 1.0 | ClCH₂CH₂Cl | ¾ | i-PrOH | 42 | 118–120.5 |
| 2-pyridyl | Me | H | —CH₂-(2-furyl) | 1.05 | ClCH₂CH₂Cl | 1¼ | i-PrOH | 75 | 149 |
| 2,3-dihydroxyphenyl | H | Me | Me | 1.1 | 95% EtOH/1.6% glacial acetic acid | 1½ | 95% EtOH | 71 | 206–207(dec) |
| 2-pyridyl | Me | H | —CH₂-(2,3,4-trimethoxyphenyl) | 1.1 | 95% EtOH/5% glacial acetic acid | 1.5 | 95% EtOH | 80 | 163–164 |
| 2-hydroxyphenyl | H | Me | Me | 1.1 | 95% EtOH/2% glacial acetic acid | 2 | 95% EtOH | 76 | 199–200(dec) |
| 4-methyl-2-hydroxyphenyl | Me | Me | Me | 1.1 | 95% EtOH/2% glacial acetic acid | 1.5 | * | 85 | 217–217.5 (dec) |
| 4-fluoro-2-hydroxyphenyl | Me | Me | Me | 1.1 | 95% EtOH/0.4% glacial acetic acid | 3.5 | * | 81 | 211–212 |

*Crystallized analytically pure from the reaction medium (b) Pharmaceutical Formulations In the following Examples, the antiviral compound is acyclovir and the RR Inhibitor is 2-acetylpyridine 4-(2-morpholinoethyl)thiosemicarbazone.

| Tablet | Amount (mg) |
|---|---|
| RR Inhibitor | 300 |
| Antiviral Compound | 200 |
| Lactose | 105 |

| Tablet | Amount (mg) |
|---|---|
| Starch | 50 |
| Polyvinylpyrrolidinone | 20 |
| Magnesium Stearate | 10 |
| | 685 |

Mix the active compounds with the lactose and starch and wet granulate with a solution of the polyvinylpyrrolidinone. Dry, sift, blend the granules with magnesium stearate and compress.

| Capsule | Amount (mg) |
| --- | --- |
| RR Inhibitor | 300 |
| Antiviral Compound | 200 |
| Lactose | 100 |
| Sodium Starch Glycollate | 10 |
| Polyvinylpyrrolidinone | 10 |
| Magnesium Stearate | 3 |
| | 623 |

Mix the active compounds with the lactose and sodium starch glycollate and wet granulate with a solution of the polyvinylpyrrolidinone. Dry, sift, blend the granules with the magnesium stearate and fill into hard gelatin capsules.

| Cream | Amount |
| --- | --- |
| RR Inhibitor | 7.5 g |
| Antiviral Compound | 5.00 g |
| Glycerol | 2.00 g |
| Cetostearyl alcohol | 6.75 g |
| Sodium Leuryl Sulphate | 0.75 g |
| White Soft Paraffin | 12.50 g |
| Liquid Paraffin | 5.00 g |
| Chlorocresol | 0.10 g |
| Purified Water to | 100.00 g |

Dissolve the active compounds in a mixture of purified water and glycerol and heat to 70° C. Add the two parts together and emulsify. Cool and fill into containers.

| Intravenous Injections | Amount |
| --- | --- |
| (1) Antiviral Compound | 200 mg |
| RR Inhibitor | 300 mg |
| Glycerol | 200 mg |
| Sodium Hydroxide solution qs | pH 7.0–7.5 |
| Water for Injections to | 10 mL |

METHOD

Dissolve the active compounds and the mannitol in a part of the Water for Injections. Adjust pH with the sodium hydroxide solution and make up to volume with additional Water for Injections. Under aseptic conditions, sterilise with solution by filtration, fill into sterile vials and remove the water by freeze-drying. Seal the vials under an atmosphere of nitrogen and close the vials with a sterile closure and a metal collar.

We claim:

1. A method of treating a topical herpes virus infection in a human also being treated with 9-(2-hydroxyethoxymethyl)guanine or a physiologically acceptable salt thereof which comprises topically applying to said human an amount of 2-acetylpyridine 5-[(dimethylamino)thiocarbamoyl]thiocarbonohydrazone sufficient to increase the antiherpes effect achievable by administering -9-(2-hydroxyethoxymethyl)guanine or said salt thereof to said human.

2. The method of claim 1 in which the herpes infection is a herpes simplex virus infection.

3. The method of claim 1 in which the herpes infection is a herpes simplex type 2 virus infection.

4. The method of claim 1 in which the herpes virus infection is a herpes varicella zoster infection.

5. The method of claim 1 in which the herpes virus infection is a herpes simplex type 1 infection.

6. The method of claim 1 in which 9-(2-hydroxethoxymethyl)guanine or its salt and the 5-[dimethylamino)-thiocarbamoy]thiocarbonohydrazone are both administered topically at the site of the infection.

* * * * *

UNITED STATES PATENT AND TRADEMARK OFFICE
CERTIFICATE OF CORRECTION

PATENT NO. : 4,758,572
DATED : July 19, 1988
INVENTOR(S) : Thomas Spector et al

It is certified that error appears in the above—identified patent and that said Letters Patent is hereby corrected as shown below:

Column 14, Claim 6, line 3, cancel "thiocarbamoy]" and insert "thiocarbamoyl]".

Signed and Sealed this

Sixth Day of December, 1988

Attest:

DONALD J. QUIGG

*Attesting Officer*   *Commissioner of Patents and Trademarks*